(12) United States Patent
Guilani et al.

(10) Patent No.: US 6,518,316 B1
(45) Date of Patent: Feb. 11, 2003

(54) CYTOKINE PRODUCTION AND TYROSINE KINASE INHIBITORS

(75) Inventors: Roya Mansour Sadeghi Guilani, Slough (GB); Stephen Keith Wrigley, Slough (GB); Sangeeta Bahl, Slough (GB); Steven Michael Martin, Slough (GB); David Andrew Kau, Slough (GB); Jenny Seugkin Tang, Slough (GB); Michael Moore, Slough (GB); David James Hardick, Slough (GB)

(73) Assignee: Xenova Limited (GB)

( * ) Notice: Subject to any disclaimer, the term of this patent is extended or adjusted under 35 U.S.C. 154(b) by 0 days.

(21) Appl. No.: 09/743,284

(22) PCT Filed: Jul. 8, 1999

(86) PCT No.: PCT/GB99/02181

§ 371 (c)(1),
(2), (4) Date: Mar. 27, 2001

(87) PCT Pub. No.: WO00/02839

PCT Pub. Date: Jan. 20, 2000

(30) Foreign Application Priority Data

Jul. 8, 1998 (GB) .............................................. 9814844

(51) Int. Cl.[7] ...................... A61K 31/12; C07C 49/587; C07C 45/00; C07C 49/215
(52) U.S. Cl. ...................... 514/680; 568/303; 568/306; 568/309; 568/312; 568/313; 568/326
(58) Field of Search .......................... 514/680; 568/303, 568/306, 309, 312, 313, 326

(56) References Cited

U.S. PATENT DOCUMENTS 5,656,644 A 8/1997 Adams et al.

OTHER PUBLICATIONS

Hashimoto T et al.: "Biologically active substances of japanese inedible mushrooms" Heterocycles, vol. 47, No. 2, (Feb. 1998) pp1067–110.

Primary Examiner—Alton Pryor
(74) Attorney, Agent, or Firm—Nixon & Vanderhye P.C.

(57) ABSTRACT

A compound of formula (I), wherein αX is =O, =N—OR[6], βNHR or βOH wherein R[6] is H or $C_1$–$C_6$ alkyl, bond a is oriented γ or δ and R is H, $C_1$–$C_6$ alkyl which is unsubstituted or substituted by $C_6$–$C_{10}$ aryl, or $C_3$–$C_6$ cycloalkyl; ε is a bond when ζ and η are not bonds or, when X is =O, ζ and η are both bonds and ε is not a bond; R[1] and R[2], which are the same or different, are H or a halogen; R[3] and R[4], which are the same or different, are H, $C_1$–$C_6$ alkyl, $C_3$–$C_6$ cycloalkyl, a heterocyclic group or an aromatic group; bond e is oriented γ or δ; and R[5] is $C_1$–$C_6$ alkyl; or formula (Ib), or formula (II), or formula (III), has activity as a cytokine production inhibitor and an inhibitor and an inhibitor of tyrosine kinase. A process for producing some of the compounds from a fungal strain, processes for producing synthetic analogues from these compounds and the use of the compounds in treating immunoinflammatory and cancerous conditions are also described.

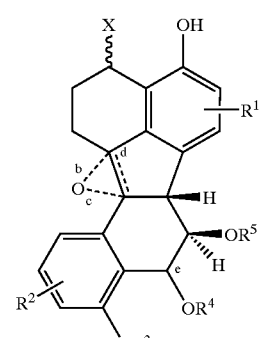

(I)

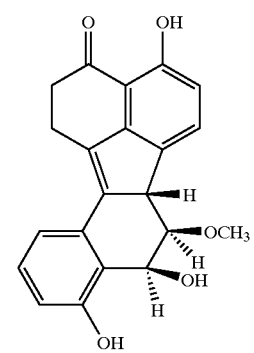

(Ib)

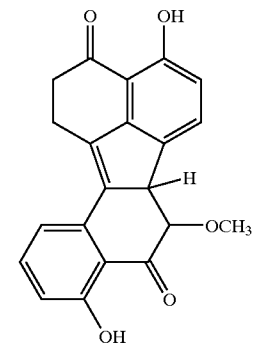

(II)

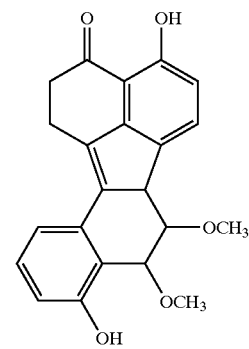

(III)

11 Claims, No Drawings

CYTOKINE PRODUCTION AND TYROSINE KINASE INHIBITORS

This application is the U.S. National Phase of PCT/GB99/02181 filed Jul. 8, 1999 which designated the United States.

The present invention relates to compounds useful as cytokine production inhibitors, to the preparation of these compounds and to pharmaceutical and veterinary compositions containing them.

It has now been found that fermentation of a strain of the fungus *Cladosporium* cf. *cladosporioides* in a nutrient medium produces biologically active novel compounds. Biologically active derivatives of those compounds, which are also novel, can be produced by standard synthetic procedures.

The present invention therefore provides a compound which is a benzofluoranthene derivative of formula (I)

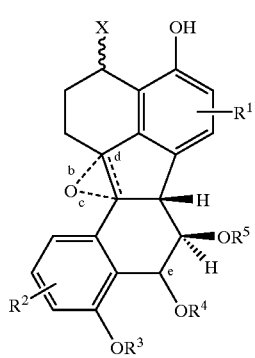

(I)

wherein ∿∿∿X is =O, =N—OR$^6$, —$^a$—NHR or —$^a$—OH wherein R$^6$ is H or $C_1$–$C_6$ alkyl, bond a is oriented ◀ or ⋯⫼⫼ and R is H, $C_1$–$C_6$ alkyl which is unsubstituted or substituted by $C_6$–$C_{10}$ aryl, or $C_3$–$C_6$ cycloalkyl;

-- $^d$ -- is a bond and -- $^b$ -- and -- $^c$ -- are not bonds or, when X is =O, -- $^b$ -- and -- $^c$ -- are both bonds and -- $^d$ -- is not a bond;

R$^1$ and R$^2$, which are the same or different, are H or a halogen;

R$^3$ and R$^4$, which are the same or different, are H, $C_1$–$C_6$ alkyl, $C_3$–$C_6$ cycloalkyl, a heterocyclic group or an aromatic group;

bond e is oriented ◀ or ⋯⫼⫼; and

R$^5$ is $C_1$–$C_6$ alkyl;

or formula (Ib):

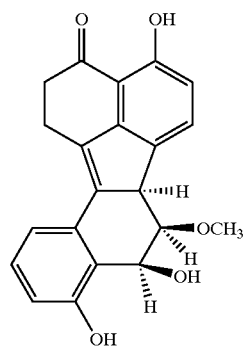

(Ib)

or formula (II)

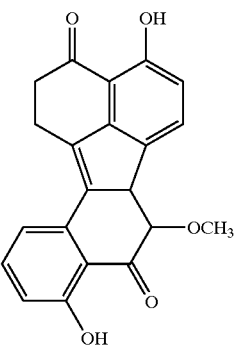

(II)

or formula (III)

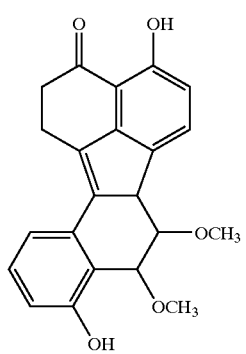

(III)

or a stereoisomer of a said derivative; or a pharmaceutically acceptable salt or ester of a said derivative or stereoisomer.

A $C_1$–$C_6$ alkyl group is straight or branched and is typically $C_1$–$C_4$ alkyl, such as methyl, ethyl, i-propyl, n-propyl, s-butyl, n-butyl or t-butyl. A $C_3$–$C_6$ cycloalkyl group may be cyclopropyl, cyclobutyl, cyclopentyl or cyclohexyl. A halogen is F, Cl, Br or I. Preferably it is Cl, Br or I.

An aromatic group is typically $C_6$–$C_{10}$ aryl. A $C_6$–$C_{10}$ aryl group may be, for instance, phenyl or naphthyl.

A heterocyclic group is a saturated or unsaturated 5- or 6-membered heterocyclic ring which contains one or more heteroatoms selected from O, N and S and which is optionally fused to a benzene ring or to a second 5- or 6-membered heterocyclic ring. The term heterocyclic group also embraces a heterocyclyl-$C_1$–$C_6$ alkyl group namely a saturated or unsaturated heterocyclic ring as defined above which is linked via a $C_1$–$C_6$ alkylene chain to the point of connection in formula (1).

A saturated heterocyclic ring may be, for example, a tetrahydrofuran, tetrahydropyran, pyrrolidine, piperidine, morpholine or piperazine group. An unsaturated heterocyclic group may be, for example, a furan, thiophene, indole, isoindole, pyrazole, imidazole, isoxazole, oxazole, isothiazole, thiazole, pyridine, quinoline, quinoxaline, isoquinoline, thienopyrazine, pyran, pyrimidine, pyridazine, pyrazine, purine or triazine group. A heterocycyl-$C_1$–$C_6$ alkyl group may be, for example, a furfuryl, pyridylmethyl, pyrrolidinylmethyl or tetrahydropyranylmethyl group.

The heterocyclic group may be unsubstituted or substituted by one or more substituents, for instance one or more substituents selected from OH, halogen $C_1$–$C_6$ alkyl which is unsubstituted or substituted, for example by halogen, such as $CF_3$, $C_1$–$C_6$ alkoxy, nitro and an amino group $N(R^{10}R^{11})$ as defined above.

In a first aspect formula (I) takes the following definitions; ⌇X is =O; $R^1$ and $R^2$ are both H, --ᵃ-- is a bond and --ᵇ-- and --ᶜ-- are not bonds; $R^3$ and $R^4$ are both H; and $R_5$ is $C_1$–$C_6$ alkyl, preferably $CH_3$.

In a second aspect of formula (I) ⌇X is —ᵃ—NHR as defined above; $R^1$ and $R^2$ are H; --ᵃ-- is a bond and --ᵇ-- and --ᶜ-- are not bonds; $R^3$ and $R^4$ are H; and $R^5$ is $C_1$–$C_6$ alkyl, preferably methyl.

In a third aspect of formula (I) ⌇X is =O; $R^1$ and $R^2$, which are the same or different, are H or halogen provided they are both H when $R^3$ is other than H; --ᵃ-- is a bond and --ᵇ-- and --ᶜ-- are not bonds; $R^3$ is H, $C_1$–$C_6$ alkyl, $C_3$–$C_6$ cycloalkyl, a heterocyclic group or an aromatic group; $R_4$ is H and $R^5$ is $C_1$–$C_6$ alkyl, preferably $CH_3$. Preferably $R^3$ is $C_1$–$C_6$ alkyl, more preferably $CH_3$.

In a fourth aspect of formula (I) ⌇X is =O; --ᵃ-- is a bond and --ᵇ-- and --ᶜ-- are not bonds; $R^1$, $R^2$ and $R^3$ are H; $R^4$ is $C_1$–$C_6$ alkyl, $C_3$–$C_6$ cycloalkyl, a heterocyclic group or an aromatic group; and $R^5$ is $C_1$–$C_6$ alkyl, preferably $CH_3$, $C_2H_5$ OR $C_3H_7$. Preferably $R^4$ is $C_1$–$C_6$ alkyl, more preferably $CH_3$.

In a fifth aspect of formula (I) ⌇X is =O or —ᵃ—OH as defined above; --ᵇ-- and --ᶜ-- are bonds and --ᵃ-- is not a bond; $R^1$, $R^2$, $R^3$ and $R^4$ are H; and $R^5$ is $C_1$–$C_6$ alkyl, preferably $CH_3$.

In formulae (I) and (Ib) bond e at position $C_8$ is preferably on the same side of the molecule as the group at position $C_7$, ($OR^5$ or $OCH_3$ respectively).

In one preferred aspect of the invention the compound is of formula (I')

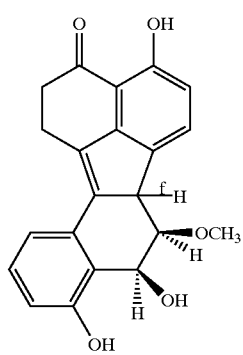

(I')

wherein bond f is oriented ◄ or ⋯⫼; or is a derivative of formula (II) or (III) as defined above.

In a more preferred aspect the compound of formula (I) is of formula (Ia):

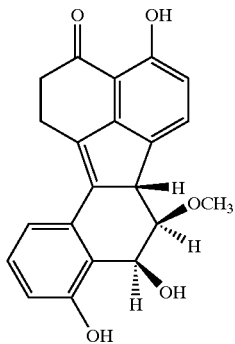

(Ia)

The stereochemical configuration shown in formulae (I), (I'),(Ia) and (Ib) as depicted above is relative, not absolute. The bonds depicted as being oriented ◄ at $C_6$, $C_7$ and $C_8$ could therefore be ⋯⫼ instead whilst those shown as ⋯⫼ could be oriented ◄ instead. Diastereoisomers of these structures represent a further aspect of the invention.

The substitution patterns of preferred compounds within formula (I) are shown in the following table:

| Compound | ⌇X | $R^1$ | $R^2$ | $R^3$ | e $OR^4$ | $R^5$ | Bond d or bonds b and c present? |
|---|---|---|---|---|---|---|---|
| Ia | =O | H | H | H | ◄OH | Me | d |
| 2 | —OH | H | H | H | ◄OH | Me | d |
| 3 | =O | H | H | H | ◄OH | Me | b and c |
| 4 | =O | H | H | Me | ◄OH | Me | d |
| 5 | ▽⌇NH | H | H | H | ◄OH | Me | d |
| 6 | ⌇NHCH$_2$Ph | H | H | H | ◄OH | Me | d |
| 7 | =N—OH | H | H | H | ◄OH | Me | d |
| 8 | =O | Cl | H | H | ◄OH | Me | d |
| 9 | =O | H | H | H | ◄OPr$_n$ | Me | d |
| 10 | =O | H | H | H | ◄OEt | Me | d |
| 11 | =O | H | H | H | ◄OMe | Me | d |
| 10a | =O | H | H | H | ⋯⫼OEt | Me | d |
| 11a | =O | H | H | H | ⋯⫼OMe | Me | d |
| 12 | =O | Br | Br | H | ◄OH | Me | d |

-continued

| Compound | ∼X | $R^1$ | $R^2$ | $R^3$ | e $OR^4$ | $R^5$ | Bond d or bonds b and c present? |
|---|---|---|---|---|---|---|---|
| 13 | =O | H | Br | H | ⎯OH | Me | d |

Some of these compounds are:

3-Cyclopropylamino-7-methoxy-1,2,3,6b, 7,8-hexahydrobenzo[d]fluoranthen-4,8,9-triol (compound 5);

3-Benzylamino-7-methoxy-1,2,3,6b,7,8-hexahydro-benzo[j]fluoranthene-4,8,9-triol (compound 6);

4,8,9-Trihydroxy-7-methoxy-1,6b,7,8-tetrahydro-2H-benzo[j]fluoranthen-3-one oxime (compound 7);

5-Chloro-4,8,9-trihydroxy-7-methoxy-1,6b,7,8-tetrahydro-2H-benzo[j]fluoranthen-3-one (compound 8);

4,9-Dihydro-7-methoxy-8-propoxy-1,6b,7,8-tetrahydro-2H-benzo[j]fluoranthen-3-one (compound 9);

8-Ethoxy-4,9-dihydroxy-7-methoxy-1,6b,7,8-tetrahydro-2H-benzo[j]fluoranthen-3-one (compound 10); and 4,9-Dihydroxy-7,8-dimethoxy-1,6b,7,8-tetrahydro-2H-benzo[j]fluroanthen-3-one (compound 11).

The compounds of formulae (Ia), (Ib), (II) and (III) above have been isolated from a fungus which has been designated Culture Collection Number X20700.

This is a fungus which was isolated directly from a dead insect which had been infected by a member of the entomogenous fungus genus *Hypocrella Sacc.* The insect was collected from tropical rainforest in Thailand during 1989. A subculture of the isolated fungus was deposited by Xenova Discovery Limited of 545 Ipswich Road, Slough, Berkshire, SL1 4EQ, United Kingdom under the Budapest Treaty at the Centraalbureau voor Schimmelcultures, Baarn, The Netherlands, on Nov. 25, 1997 under reference X15/81/700. It was assigned the accession number CBS 100220.

The fungal strain CBS 100220 is a hyphomycete assigned to the widespread genus Cladosporium Link ex Fr. and no sexually reproducing state was observed in culture. Cultures incubated at 24° C. had relatively slowly extending mycelium which attained 6–7 mm diameter after 7d on both 2% MEA and potato/carrot (PCA) agar. No growth was observed on these media at 37° C. The recipes for MEA and PCA are given in Smith, D. & Onions, A. H. S., 1983; The Preservation and Maintenance of Living Fungi. Farnham Royal: CABI (using 20 g not 2 g of grated carrot).

Macroscopic characteristics were as follows:

| Characters | MEA 24° C. | PCA 24° C. |
|---|---|---|
| Mycelial texture | Abundant dense aerial mounds | Low sparse aerial mycelium |
| Main mycelial colours* above | Olivaceous buff to grey olivaceous | Grey olivaceous to sepia |
| Main mycelial colours* below | Olivaceous black to fuscous black | Sepia to fuscous black |
| Main colours* of aerial droplets | 9H (ochreous) | None observed |

*Colours according to Flora of British Fungi: Colour Identification Chart, 1969, HMSO, Edinburgh, UK.

Generally, all cultures sporulated very sparsely within the aerial mycelium. Mycelial margins were submerged on both media whereas the central regions were radially sulcate on MEA only.

Microscopically, the conidiophores were usually septate with thick brown walls at their base tapering and becoming progressively thinner-walled and paler towards their apices. The apices were usually slightly swollen at the point of attachment of the lowermost conidia (ramo-conidia). Ramo-conidia were very rarely 1-septate and formed the main branches of a loose head of branched acropetally extending chains of aseptate conidia with apiculate ends.

Microscopic characters were as follows:

| | |
|---|---|
| Conidiophore length ($\mu$) | 19–240 |
| Max. conidiophore width ($\mu$) | <5 |
| Conidial form | Mostly smooth, fusiform or limoniform |
| Ramo-conidial length ($\mu$) | <16 |
| Ramo-conidial width ($\mu$) | 2.5–4.0 |
| Conidial length ($\mu$) | 3–6.5 |
| Conidial width ($\mu$) | 1.5–3.5 |

Although the fungus exhibits most of the characters of *Cladosporium cladosporicides* (Fres.) de Vries, nevertheless it has a slower mycelial extension rate and much sparser conidiogeniesis than usually encountered within this taxon. Furthermore, four other isolates originating from similar source material (two collected during the following year in 1990) had characters consistent with the above details. Hence this fungus has been assigned to *Cladosporium* cf. *cladosporioides.*

The above description is illustrative of a strain of *Cladosporium* cf. *cladosporioides* which can be employed in the production of compounds of the present invention. However, the present invention also embraces mutants of the above described microorganism. For example, those which are obtained by natural selection or those produced by mutating agents including ionising radiation such as ultraviolet irradiation, or chemical mutagens such as nitrosoguanidine or the like treatments, are also included within the ambit of this invention.

The present invention further provides a process for producing a compound of formula (I'), (Ia), (Ib), (II) or (III) as defined above, which process comprises (i) fermenting, in a fermentation medium which provides a source of carbon, nitrogen and inorganic salts, fungal strain X20700 (CBS 100220) or a mutant thereof which produces a said compound; and (ii) isolating the said compound from the fermentation medium.

The invention also provides a biologically pure culture of the fungal strain *Cladosporium* cf. *cladosporioides* X20700 (CBS 100220) or a mutant thereof which produces a compound of formula (I') (Ia), (Ib), (II) or (III) as defined above. Such cultures are substantially free from other microorganisms. The invention further provides a process for fermenting the fungal strain *Cladosporium* cf. *cladosporioides* X20700 (CBS 100200) which process comprises fermenting the said fungal strain or said mutant in a fermentation medium which provides a source of carbon, nitrogen and inorganic salts.

Assimilable sources of carbon, nitrogen and minerals may be provided by either simple or complex nutrients. Sources of carbon will generally include glucose, maltose, starch, glycerol, molasses, dextrin, lactose, sucrose, fructose, carboxylic acids, amino acids, glycerides, alcohols, alkanes and vegetable oils. Sources of carbon will generally comprise from 0.5 to 10% by weight of the fermentation medium.

Sources of nitrogen will generally include soya bean meal, corn steep liquors, distillers' solubles, yeast extracts, cottonseed meal, peptones, ground nut meal, malt extract, molasses, casein, amino acid mixtures, ammonia (gas or solution), ammonium salts or nitrates. Urea and other amides may also be used. Sources of nitrogen will generally comprise from 0.1 to 10% by weight of the fermentation medium.

Nutrient mineral salts which may be incorporated into the culture medium include the generally used salts capable of yielding sodium, potassium, ammonium, iron, magnesium, zinc, nickel, cobalt, manganese, vanadium, chromium, calcium, copper, molybdenum, boron, phosphate, sulphate, chloride and carbonate ions.

An antifoam may be present to control excessive foaming and is added at intervals as required.

Fermentation can be conducted at temperatures ranging from 20° C. to 40° C., preferably 24–30° C. For optimal results, it is most convenient to conduct these fermentations at a temperature in the range 24–26° C. The starting pH of the nutrient medium suitable for producing the compounds can vary from 5.0 to 8.5 with a preferred range of from 5.0 to 7.5.

Small scale fermentations are conveniently carried out by placing suitable quantities of nutrient medium in a flask by known sterile techniques, inoculating the flask with either spores or vegetative cellular growth of the fungal strain, loosely stoppering the flask with cotton wool, and permitting the fermentation to proceed in a constant room temperature of about 25° C. on a rotary shaker at from 95 to 300 rpm for 2 to 10 days. The fermentation may also be conducted in static culture on liquid or semi-solid medium.

For larger scale work, it is preferable to conduct the fermentation in suitable tanks provided with an agitator and a means of aerating the fermentation medium. The nutrient medium is made up in the tank after sterilization and is inoculated with a source of vegetative cellular growth of the fungal strain. The fermentation is usually allowed to continue for from 1 to 10 days while agitating and/or aerating the nutrient medium at a temperature in the range 20° C. to 37° C. The degree of aeration is dependent upon several factors such as the size of the fermenter and agitation speed. Generally the larger scale fermentations are agitated at about 95 to 750 rpm and aerations of about 0.5 to 1.5 VVM (volumes of air per volume of medium per minute).

The separation of the compounds of formulae (Ia), (Ib), (II) and (III) from the whole fermentation broth and their recovery is carried out by solvent extraction followed by application of chromatographic fractionations with various chromatographic techniques and solvent systems. The present compounds in pure form have thus been isolated in this way.

The compound of formula (Ia) can be used as a starting material for the synthesis of structural analogues which are also biologically active. Accordingly, the present invention further provides a process for producing a compound as defined above, which process comprises:

(a) treating a compound of formula (Ia)

(Ia)

with an amine of formula R'—$NH_2$ in which R' is H, $C_1$–$C_6$ alkyl which is unsubstituted or substituted by $C_6$–$C_{10}$ aryl, or $C_3$–$C_6$ cycloalkyl, in water or an organic solvent in the presence of a reducing agent at a pH of from 5 to 6, to obtain a compound of formula (I) in which ⌇X is a —ᵃ—NHR as defined above; or (b) treating a compound of formula (Ia) as defined above with a halogenating agent to obtain a compound of formula (I) in which one or both of $R^1$ and $R^2$ is a halogen; or (c) treating a compound of formula (Ia) as defined above with an alcohol of formula $R^{41}$—OH in which $R^{41}$ is as defined above for $R^4$, other than hydrogen, in the presence of an acid, to obtain a compound of formula (I) in which $R^4$ is as defined for $R^{41}$; or (d) treating a compound of formula (Ia) as defined above with a halide of formula $R^{31}$—Y in which Y is a halogen and $R^{31}$ is as defined above for $R^3$, other than hydrogen, in an organic solvent in the presence of a base and, optionally, a quaternary ammonium halide to obtain a compound of formula (I) in which $R^3$ is as defined above for $R^{31}$; or (e) treating a compound of formula (Ia) as defined above with hydroxylamine in an organic solvent and/or water to obtain a compound of formula (I) in which ⌇X is =N—OH; or (f) treating a compound of formula (Ia) as defined above with a peracid in an organic solvent to give a compound of formula (I) in which --ᵇ-- and --ᶜ-- are both bonds and --ᵈ-- is not a bond; or (g) treating a compound of formula (Ia) as defined above with a reducing agent in an organic solvent to give a compound of formula (I) in which ⌇X is —ᵃ—OH as defined above; or (h) treating a compound of formula (Ia) as defined above with an oxidising agent in to obtain a compound of formula (II) as defined above in which the groups —H and —$OCH_3$ are both oriented ◂, and/or, if desired;

(i) converting a compound obtained in any one of steps (a) to (h) into a pharmaceutically acceptable salt or ester.

Process embodiment (a) is a reductive amination. The reducing agent may be. for example, sodium borohydride or sodium cyanoborohydride. The solvent may be water or an organic solvent which is preferably a polar protic solvent such as an alcohol, for instance methanol or ethanol. The process typically comprises dissolving the compound of formula (Ia) in the organic solvent and then adding the amine R'—NH to the resulting solution, followed by stirring at about 25° C. for 5 to 30 minutes. The reducing agent is then added and the pH of the solution is adjusted to within the desired range by using a drop of bromocresol green in the reaction. The reaction solution may then be concentrated in vacuo and the residue taken up in a suitable organic solvent, for instance dichloromethane or ethyl acetate, and then extracted with water and saturated brine.

In process embodiment (b) the halogenating agent and the reaction conditions are chosen according to whether mono- or di-halogenation is required. To produce a compound of formula (I) in which $R^1$ is a halogen and $R^2$ is hydrogen the halogenating agent is typically a thionyl halide, for instance thionyl chloride or thionyl bromide. The reaction may be conducted at a temperature of about 25° C. for a period of from 1 to 8 hours, preferably about 4 hours. To produce a compound of formula (I) in which both $R^1$ and $R^2$ are a halogen, or $R^2$ is a halogen and $R^1$ is hydrogen, the halogenating agent is typically an N-halosuccinimide such as N-chlorosuccimimide, N-bromosuccinimide or N-iodosuccinimide. The reaction is generally conducted in an organic solvent such as a halogenated hydrocarbon, for instance dichloromethane, at a temperature of about 25° C. for a period of from 3 to 16 hours.

In process embodiment (c) the compound of formula (Ia) is usually dissolved in the alcohol $R^{41}$—OH, and the acid is then added dropwise. The acid is generally a concentrated mineral acid such as $H_2SO_4$. The reaction mixture is then stirred from 25° C. for a period of from 1 to 5 hours, preferably about 2 hours, and may then be neutralised with an alkali such as sodium hydroxide. The desired ether product may then be extracted and purified by conventional methods, for instance by preparative HPLC.

In process emobodiment (d) the halide of formula $R^{31}$—Y is preferably an iodide and the quaternary ammonium halide is preferably a quaternary ammonium iodide such as tetrabutylammonium iodide. The organic solvent is typically an aprotic solvent such as dimethylformamide, acetonitrile or a halogenated hydrocarbon such as dichloromethane and the base may be, for instance, an alkali metal carbonate such as potassium carbonate or sodium carbonate. The process is generally conducted by dissolving the compound of formula (Ia) in the solvent and then adding thereto the quaternary ammonium salt (trace) followed by the halide. The reaction is then stirred with a saturated solution of the base for a period of 1 to 6 hours, preferably about 2 hours. A further amount of the halide may then be added, if desired or necessary, and the stirring continued. The reaction mixture is then typically acidified, for instance with a strong mineral acid such as HCl or $H_2SO_4$, to a pH of about 1. The solvent phase may be separated off and the desired product recovered.

In process embodiment (e) the reaction may be carried out using a salt of hydroxylamine such as hydroxylamine hydrochloride in the presence of sodium hydroxide. The hydroxylamine then reacts as it is released from its salt. The hydroxylamine hydrochloride is typically dissolved in aqueous sodium hydroxide and the pH is adjusted to about 5. The compound of formula (Ia) dissolved in the organic solvent is then added to the solution. The organic solvent is typically an alcohol such as methanol or ethanol. The reaction mixture may be left to stir at a temperature of about 25° C. for a period of from 1 hour to 24 hours until the reaction is complete.

Process embodiment (f) involves epoxide formation at the olefinic double bond. The compound of formula (Ia) is typically dissolved in the organic solvent, which may for instance be a halogenated hydrocarbon such as chloroform, and the peracid is added to the resulting solution. Examples of suitable peracids include m-chloroperbenzoic acid and peracetic acid. The reaction mixture is usually stirred at a temperature of about 25° C. for a period of from 0.5 to 3 hours to allow the reaction to proceed to completion. The solvent may then be removed and the product purified.

In process embodiment (g) the compound of formula (Ia) is usually dissolved in the organic solvent and the reducing agent then added to the resulting solution. The solvent is preferably an alcohol such as methanol or ethanol. The reducing agent is chosen from those which are suitable for the reduction of ketones to alcohols, such as $LiAlH_4$, $LiBH_4$, $NaBH_4$ and $KBH_4$. $NaBH_4$ is preferred. The reaction mixture is usually left for about 1–2 hours at 25° C. before destroying excess reducing agent, for example by adding a few drops of glacial acetic acid. The crude product may then be concentrated In vacuo and purified by conventional means.

Process embodiment (h) is generally carried out by dissolving compound (Ia) in the organic solvent, adding the oxidising agent to the resulting solution and then stirring the reaction mixture at a temperature of about 25° C. for a period of from 5 hours to 30 hours, preferably about 24 hours. The solvent is typically a halogenated hydrocarbon such as dichloromethane. The oxidising agent may be any such agent which is suitable for the oxidation of a secondary alcohol to a ketone, for instance manganese dioxide. The reaction mixture is typically filtered and the product purified following completion of the reaction.

Compounds of formula (I) may be converted into pharmaceutically acceptable salts, and salts may be converted into the free compound, by conventional methods. Suitable salts include salts with pharmaceutically acceptable, inorganic or organic bases. Examples of inorganic bases include ammonia and carbonates, hydroxides and hydrogen carbonates of group I and group II metals such as sodium, potassium, magnesium and calcium. Examples of organic bases include aliphatic and aromatic amines such as methylamine, triethylamine, benzylamine, dibenzylamine or α- or β-phenylethylamine, amino acids such as arginine, and heterocyclic bases such as piperidine, 1-methylpiperidine and morpholine.

Compounds of formula (I) may also be converted into pharmaceutically acceptable esters. Suitable esters include branched or unbranched, saturated or unsaturated $C_1$–$C_6$ alkyl esters, for example methyl, ethyl and vinyl esters.

The compounds of formulae (I), (II) and (III) are inhibitors of the production of cytokines, specifically IL-2. They are also tyrosine kinase inhibitors. These compounds can therefore be used in the treatment of immunoinflammatory conditions. A human or animal, e.g. a mammal, can therefore be treated by a method comprising administration of a therapeutically effective amount of a compound of formula (I), (II) or (III). These compounds can be used in the treatment of immunoinflammatory conditions such as rheumatoid arthritis, osteoarthritis, septic shock, psoriasis, inflammatory bowel disease, Crohn's disease and asthma, and for the prevention of organ transplant rejection. As tyrosine kinase inhibitors, the compounds of formulae (I), (II) and (III) can be used in the treatment of cancer such as leukemia, malignant melanoma, liver cancer, colon cancer or breast cancer.

The compounds of the present invention can be administered in a variety of dosage forms, for example orally such as in the form of tablets, capsules, sugar- or film-coated tablets, liquid solutions or suspensions or parenterally, for example intramuscularly, intravenously or subcutaneously. The present compounds may therefore be given by injection or infusion.

The dosage depends on a variety of factors including the age, weight and condition of the patient and the route of administration. Typically, however, the dosage adopted for each route of administration for adult humans is 0.001 to 10 mg/kg, most commonly in the range of 0.01 to 5 mg/kg, body weight. Such a dosage may be given, for example, from 1 to 5 times daily orally or by bolus infusion, infusion over several hours and/or repeated administration.

The toxicity of the compounds of the invention is negligible so they can safely be used in therapy.

The compounds of the present invention are formulated for use as a pharmaceutical or veterinary composition also comprising a pharmaceutically or veterinarily acceptable carrier or diluent. The compositions are typically prepared following conventional methods and are administered in a pharmaceutically or veterinarily suitable form.

For example, the solid oral forms may contain, together with the active compound, diluents, such as lactose, dextrose, saccharose, cellulose, corn starch or potato starch; lubricants such as silica, talc, stearic acid, magnesium or calcium stearate and/or polyethylene glycols; binding agents such as starches, arabic gums, gelatin, methylcellulose, carboxymethylcellulose, or polyvinyl pyrrolidone; disintegrating agents such as starch, alginic acid, alginates or sodium starch glycolate; effervescing mixtures; dye-stuffs; sweeteners; wetting agents such as lecithin, polysorbates, laurylsulphates. Such preparations may be manufactured in known manner, for example by means of mixing, granulating, tabletting, sugar coating, or film coating processes.

Liquid dispersions for oral administration may be syrups, emulsions and suspensions. The syrups may contain as carrier, for example, saccharose or saccharose with glycerol and/or mannitol and/or sorbitol. In particular a syrup for diabetic patients can contain as carriers only products, for example sorbitol, which do not metabolise to glucose or which only metabolise a very small amount to glucose. The suspensions and the emulsion may contain a carrier, for example a natural gum, agar, sodium alginate, pectin, methylcellulose, carboxymethylcellulose or polyvinyl alcohol.

Suspensions or solutions for intramuscular injections may contain, together with the active compound, a pharmaceutically acceptable carrier such as sterile water, olive oil, ethyl oleate, glycols such as propylene glycol, and if desired, a suitable amount of lidocaine hydrochloride. Solutions for intravenous injection or infusion may contain a carrier, for example, sterile water which is generally Water for Injection. Preferably, however, they may take the form of a sterile, aqueous, isotonic saline solution.

Alternatively, the compounds of the present invention may be encapsulated within liposomes.

The following examples illustrate the invention

EXAMPLE 1

Batch Fermentation of *Cladosporium* cf. *cladosporioides*. 20700

Starting material of the strain *Cladosporium* cf. *cladosporioides* was generated by suspending a mature slant culture, grown on a nutrient agar slope Al (2% malt extract, 0.1% peptone, 2% glucose, 1.5% agar), in 5 ml 10% aqueous glycerol. 1 ml of this suspension, in a 1.5 ml cryovial, comprises the starting material which was retrieved from storage at −135° C. A preculture was produced by aseptically placing 1 ml of starting material in 10 ml nutrient solution S1 (2% malt extract, 0.1% peptone, 2% glucose, adjusted to pH 6.0) and incubating for 10 days at 25° C.

An intermediate culture was generated by aseptically transferring the preculture into a 250 ml flask containing 40 ml of nutrient solution S2 (1.5% glycerol, 1.5% soya bean peptone, 1% D-glucose, 0.5% malt extract, 0.3% NaCl, 0.1% CaCO3, 0.1% Tween 80, 0.1 Junlon PW110, (supplied by Honeywell and Stein Ltd., Sutton, Surrey, U.K.) adjusted to pH 6.0) shaken at 240 rpm for 3 days at 25° C.

The seed culture was generated by aseptically transferring the intermediate culture into 2 liters of nutrient solution S2 in a 3L fermenter. The 3L fermenter was agitated at 500 rpm, aerated at 1 liter per minute, and controlled at 25° C. for 3 days.

A production culture was generated by aseptically transferring the seed culture to a 75L fermenter containing 50L of nutrient solution P (2.6% trehalose, 0.5% yeast extract, 0.975% MES buffer, 0.1% Tween 80, 0.1% carboxymethylcellulose 0.1%, antifoam A 0.1%, adjusted to pH 6.0). The production fermenter was stirred at 350 rpm, aerated at 25 liters per minute, and the temperature controlled at 25° C. for 9 days, at which point the production culture was harvested.

The harvested production culture was separated into liquor and biomass by passing the culture broth through a disc-stack centrifuge.

EXAMPLE 2

Extraction and Purification of Compounds (Ia), (Ib) and (II)

The broth of Example 1 was harvested by centrifugation using a Westfalia disc stack centrifuge. The clarified liquor was discarded and the biomass retained for extraction. The biomass (approximately 10L by volume) was carefully transferred into a 30L mixing vessel, to which 20L of an acetone/methanol (1:1) solvent mix was added and the contents stirred for 3 hours after which the contents of the vessel were emptied and filtered through a 20L Buchner funnel. The filtered solvent extract was retained and the retentate (biomass) was transferred back to the mixing vessel and charged with a further 20L of methanol and extracted for 3 hours. The contents of the mixing vessel were emptied and filtered through the Buchner funnel. The solvent extract was pooled with the first extract to give a volume of approximately 40L.

The solvent extract was evaporated to an aqueous residue using a LUWA thin film evaporator. The aqueous fraction (5L) was then back extracted with 4×5L of ethyl acetate (20 minutes per extraction). The solvent extracts were pooled, dried with sodium sulphate and evaporated to low volume (200 ml) under reduced pressure. The extract was then dried onto 40 g of loose silica gel under reduced pressure and then fractionated by normal phase flash chromatography using a Biotage Flash 75L system with a SIM 500 module for sample introduction and a 10×30 cm Hyperprep Kpsil 32–62 μm 60 Å prepacked cartridge using a stepwise gradient elution method. Initially the column was eluted with 100% hexane, then the gradient proceeded from 100% hexane to 100% ethyl acetate in 10% increments, with each step consisting of a 1L volume. A final wash of 90% ethyl acetate:10% methanol was used for cleaning purposes. The fractions generated were analysed by HPLC and those containing the target compounds were evaporated to dryness and resuspended in 20 to 60 ml of methanol. Compound (Ia) was eluted with 80 to 90% ethyl acetate. Compound (II) eluted with 40% ethyl acetate, Compound (Ib) with 50% ethyl acetate, and compound (III) with 60% ethyl acetate.

Compound (Ia) was purified by preparative reversed phase high-performance liquid chromatography (HPLC) using a Biotage KP100 HPLC system with a 10×300 mm Shandon hyperprep HS Bos 100 Å 12 μm C18 prepacked column and an isocratic mobile phase (60% water:40% acetonitrile) with a flow rate of 350 ml/min and dual wavelength UV detection at 300 nm and 400 nm. The peak collected after 9 minutes was evaporated to an aqueous phase and then freeze dried yielding a total of 1.4 g of compound (Ia).

Compounds (Ib) and (II) were purified by preparative reversed phase HPLC using a Waters Delta Prep HPLC system with a 40×200 mm Prep NovaPak 60 Å 6 μm C18 column and isocratic mobile phases comprising 52% water:48% acetonitrile for compound (Ib) and 30% water:70% acetonitrile for compound (II). The flow rate was 55 ml/min and UV detection was at 340 nm. Compound (Ib) eluted after 8 to 8.5 minutes and compound (II) eluted after 6 to 6.5 minutes, both compounds were evaporated to an aqueous phase and then freeze dried to yield 20 mg of Compound (Ib) and 40 mg of compound (II).

Compound (III) was purified by semi-preparative reversed phase chromatography employing a 25×200 mm Prep NovaPak 60 Å 6 μm C18 column eluted with an isocratic mobile phase comprising 55% water:45% acetonitrile. The flow rate was 20 ml/minute and the column eluate was monitored at a wavelengtn of 300 nm. The peak eluted at 13.5 minutes was collected, evaporated to an aqueous phase and then freeze dried to yield 12 mg of compound (III).

Physicochemical, $^1$H nmr and $^{13}$C nmr data for the four compounds are set out in Tables 1 to 3 below.

TABLE 1

Physico-chemical Properties

| | (Ia) | (Ib) | (II) | (III) |
|---|---|---|---|---|
| DCI-MS (m/z) | 351 (MH$^+$) 333 ([MH-H$_2$O]$^+$) | 351 (MH$^+$) 333 ([MH-H$_2$O]$^+$) | | |
| DEI-MS (m/z) | 350 (M$^+$) 332 ([M-H$_2$O]$^+$) | 350 (M$^+$) 332 ([M-H$_2$O]$^+$) | 348 (M$^+$) | 364 (M$^+$) |
| Molecular formula | C$_{21}$H$_{18}$O$_5$ | C$_{21}$H$_{18}$O$_5$ | C$_{21}$H$_{16}$O$_5$ | C$_{22}$H$_{26}$O$_5$ |
| UV-vis $\lambda_{max}$ /nm (MeOH) | 212, 255, 307, 382 | 212, 255, 307, 382 | 240, 271, 290, 304, 401 | 212, 355, 307, 382 |
| IR (KBr) v/cm$^{-1}$ | 3423, 2927, 2854, 1706, 1641, 1605, 1579, 1470, 1345, 1277, 1229, 1194 1118, 1094 | 3273, 2913, 2844, 1701, 1645, 1604, 1569, 1445, 1410, 1348, 1325, 1275, 1209, 1190, 1161, 1130, 1125, 1071, 1008 | 2962, 2927, 2858, 2830, 1708, 1645, 1604, 1555, 1458, 1348, 1334, 1275, 1195, 1161 | 3245, 3052, 2934, 2823, 1632, 1569, 1458, 1327, 1271, 1223, 1188, 1091, 1043, 731 |

TABLE 2

$^1$H NMR assignment

| | $\delta_w$/ppm in CDCl$_3$* | |
|---|---|---|
| Position | Ia | Ib |
| 1 | 3.35(2H, m) | 3.40(2H, m) |
| 2 | 2.88(2H, m) | 2.90(2H, m) |
| 3 | | |
| 3a | | |
| 4 | 10.6(1H, s, OH) | 0.69(1H, s, OH) |
| 5 | 6.76(1H, d, 8.1) | 6.76(1H, d, 8.2) |
| 6 | 7.70(1H, d, 8.2) | 7.63(1H, d, 8.2) |
| 6a | | |
| 6b | 3.99(1H, dt, 11.9, 2.4) | 3.78(1H, bd, 2.2) |
| 7 | 3.22(1H, dd, 11.9, 4.2) | 4.51(1H, dd, 4.2, 2.0) |
| 8 | 5.39(1H, d, 4.1) | 5.23(1H, dd, 10.7, 3.8) 3.52(1H, bd, 11.3, OH) |
| 8a | | |
| 9 | | 8.77(1H, s, OH) |
| 10 | 6.91(1H, d, 8.0) | 6.90(1H, dd, 8.0, 1.0) |
| 11 | 7.30(1H, d, 7.9) | 7.27(1H, t, 7.9) |
| 12 | 7.21(1H, d, 7.8) | 7.20(1H, dd, 7.0, 1.0) |

TABLE 2-continued

$^1$H NMR assignment

| | | |
|---|---|---|
| 12a | | |
| 12b | | |
| 12c | | |
| 12d | | |
| 1' | 3.55(3H, s) | 3.08(3H, s) |
| 2' | | |

| | $\delta_w$/ppm in CDCl$_3$* | |
|---|---|---|
| Position | II | III |
| 1 | 3.35(2H, m) | 3.25(2H, m), 3.35(1H, m) |
| 2 | 2.95(2H, m) | 2.85(2H, m) |
| 3 | | |
| 3a | | |
| 4 | 10.6(1H, s, OH) | 10.6(1H, s, OH) |
| 5 | 6.85(1H, d, 8.3) | 6.75(1H, d, 8.2) |
| 6 | 7.70(1H, d, 8.2) | 7.80(1H, d, 8.2) |
| 6a | | |
| 6b | 4.15(1H, dt, 12.7, 2.4) | 4.30(1H, dt, 11.8, 2.5) |
| 7 | 3.55(1H, d, 12.7) | 3.15(1H, dd, 11.8, 3.5) |
| 8 | | 5.20(1H, d, 3.5) |
| 8a | | |
| 9 | 12.2(H, s, OH) | |
| 10 | 6.90(1H, d, 8.3) | 6.8(1H, dd, 6.9, 2.0) |
| 11 | 7.50(1H, t, 8.0) | 7.25(1H, m) |
| 12 | 7.1(1H, d, 7.4) | 7.25(1H, m) |
| 12a | | |
| 12b | | |
| 12c | | |
| 12d | | |
| 1' | 3.75(3H, s) | 3.55(3H, s) |
| 2' | | 3.70(3H, s) |

*Coupling constants given in Hz in parentheses

TABLE 3

13C NMR assignments $\delta_c$/ppm in CDCl$_3$

| Position | (Ia) | (Ib) | (II) | (III) |
|---|---|---|---|---|
| 1 | 22.8 | 23.1 | 22.9 | 23.1 |
| 2 | 36.5 | 36.6 | 36.3 | 36.5 |
| 3 | 201.7 | 201.9 | 201.3 | 201.8 |
| 3a | 112.4 | 112.7 | 112.7 | 112.2 |
| 4 | 159.2 | 159.5 | 159.6 | 159.1 |
| 5 | 113.5 | 112.9 | 114.5 | 113.4 |
| 6 | 133.0 | 130.3 | 132.9 | 133.5 |
| 6a | 132.9 | 132.1 | 134.0* | 133.6 |
| 6b | 49.6 | 53.9 | 55.2 | 50.7 |
| 7 | 82.0 | 81.1 | 85.0 | 83.8 |
| 8 | 63.9 | 70.8 | 284.1 | 71.4 |
| 8a | 123.0 | 120.6 | 114.3 | 122.7 |
| 9 | 156.6 | 158.3 | 163.4 | 155.5 |
| 10 | 116.2 | 117.2 | 117.6 | 115.1 |
| 11 | 130.1 | 129.5 | 137.1 | 129.8 |
| 12 | 118.5 | 118.0 | 117.0 | 118.9 |
| 12a | 133.1 | 131.7 | 137.5 | 134.4 |
| 12b | 139.9 | 138.2 | 136.0 | 140.5 |
| 12c | 131.3 | 131.0 | 133.8* | 131.3 |
| 12d | 150.9 | 151.7 | 150.1 | 150.5 |
| 1' | 58.1 | 61.8 | 60.6 | 57.8 |
| 2' | — | — | — | 58.9 |

*Assignments interchangeable

EXAMPLE 3

Synthesis of Compound 2 ($C_{21}H_{20}O_5$)

Compound (Ia) (8.7 mg, 0.025 mmol) was dissolved in absolute ethanol (2 mL) to give a yellow coloured solution. Sodium borohydride (12 mg, 0.32 mmol) was added to this solution, whereupon the colour of the reaction changed from yellow to a pale pink. After 1.5 h at 25° C., three drops of glacial acetic acid were added from a Pasteur pipette to destroy excess sodium borohydride.

The reaction was then concentrated in vacuo to give an opaque oil. To remove the borate salts, this oil was repeatedly dissolved in methanol and the solvent evaporated in vacuo to eventually give a white, crystalline solid. Purification of the crude product was carried out by HPLC (C18 column, 2.5×30 cm, 25% acetonitrile/water, 25 mL/min., detection at 320 nm) followed by lyophilisation.

Two diastereoisomers were isolated.
major (isomer 2a)
7.4 min., 6.3 mg (72%)
$^1$H NMR (400 MHz, d4-MeOH) δ 7.44 (1H, d, 8.1), 7.29–7.25 (2H, m), 6.85–6.79 (1H, m), 6.68 (1H, d, 8.0), 5.59 (1H, d, 3.3), 5.32 (1H, dd, 8.0, 4.0), 4.10 (1H, br.d, 11.7), 3.59 (3H, s) 3.10–3.03 (3H, m), 2.30–2.20 (1H, m), 2.12–2.01 (1H, m); MS (accurate mass DEI), found 352.1301 M$^+$, calculated for $C_{21}H_{20}O_5$, 352.1311.
minor (isomer 2b)
5.4 min., 2.1 mg (24%)
$^1$H NMR (400 MHz, d4-MeOH) δ 7.48 (1H, d, 7.8), 7.29 (1H, t, 7.8), 7.22 (1H, br.d, 7.8), 6.84 (1H, br.d, 7.9), 6.71 (1H, d, 8.0), 5.60 (1H, d, 3.4), 5.26 (1H, t, 3.4), 4.00 (1H, dt, 11.8, ~1.0), 3.59 (3H, s), 3.23–3.12 (1H, m), 3.08 (1H, dd, 11.7, 3.4), 3.00–2.91 (1H, m), 2.34–2.26 (1H, m), 1.93–1.83 (1H, m); MS (accurate mass DEI), found 352.1304 M$^+$, calculated for $C_{21}H_{20}O_5$ 352.1311.

EXAMPLE 4

Synthesis of Compound 3 ($C_{21}H_{18}O_6$)

Compound (Ia) (10 mg, 0.028 mmol) was dissolved in chloroform (3 mL, slowly soluble) and to this solution meta-chloroperbenzoic acid (10 mg of 57–86% hydrated solid, ca. 0.033 mmol) was added. The reaction was stirred for 1 h at 25° C. before removal of the solvent in vacuo and purification by HPLC. Analytical HPLC of the reaction (C18 column, 0.8×10 cm, 40% acetonitrile/water, 2 mL/min., PDA detection) gave product (3.34 min.) and starting material (4.93 min).

Preparative HPLC conditions: (C18 column, 2.5×30 cm, 38% acetonitrile/water, 25 mL/min., detection at 220 nm). Pure fractions were concentrated and then lyophilised to give the epoxide, 2.3 mg, 22%.
$^1$H NMR (400 MHz, CDCl$_3$) δ 10.62 (1H, s), 7.65 (1H, d, 8.4), 7.28–7.23 (1H, m), 6.94 (1H, d, 7.5), 6.89 (1H, d, 8.4), 6.85 (1H, d, 8.3), 5.28 (1H, d, 3.5), 3.79 (1H, d, 10.2), 3.48 (3H, s), 3.25 (1H, dd, 10.1, 3.5), 3.20–3.13 (1H, m), 3.11–3.02 (1H, br.s), 2.89–2.80 (1H, m), 2.62 (1H, td, 14.8, 5.0), 2.43 (1H, ddd, 14.8, 5.9, 1.9); MS (accurate mass, DEI) found 366.1076 M$^+$, calculated for $C_{21}H_{18}O_6$ 366.1103, also 348.0985 (M$^+$ minus H$_2$O), calculated for $C_{21}H_{16}O_5$ 348.0998.

EXAMPLE 5

Synthesis of Compound 4 ($C_{22}H_{16}O_5$)

Compound (Ia) (9.5 mg, 0.027 mmol) was dissolved in dichloromethane (4 mL) and to this was added tetrabutylammonium iodide (trace) followed by methyl iodide (100 μL, 1.6 mmol). The reaction was then stirred vigorously with aqueous potassium carbonate solution (2 mL of a saturated solution) for 2 h. After this time, a further aliquot of methyl iodide (100 μL) was added to the reaction and stirring was continued for another 3 h at 25° C. The reaction was then acidified to pH 1 with aqueous HCl solution (1M) and the dichloromethane phase was separated off. This organic fraction was washed with saturated aqueous sodium thiosulfate solution, dried (MgSO$_4$), filtered and concentrated in vacuo.

Analytical HPLC of the reaction (C18 column, 0.8×10 cm, 55% acetonitrile/water, 2 mL/min., PDA detection) gave product (4.26 min.) with no evidence of any starting material. Preparative HPLC was carried out under the following conditions: C18 column, 2.5×30 cm, 55% acetonitrile/water, 25 mL/min., detection at 220 nm. The product was obtained as a bright yellow powder, 5.1 mg (51%, following lyophilisation.

$^1$H NMR (400 MHz, CDCl$_3$) δ 10.61 (1H, s), 7.76 (1H, d, 8.2), 7.38 (1H, t, 8.0), 7.25 (1H, d, 8.0), 6.89 (1H, d, 8.2), 6.75 (1H, d, 8.2), 5.54 (1H, d, 3.4), 4.20 (1H, dt, 11.7, 2.4), 3.94 (3H, s), 3.54 (3H, s), 3.45–3.33 (1H, m), 3.30–3.20 (1H, m), 3.17 (1H, dd, 11.7, 3.5), 2.96–2.79 (3H, m); MS (accurate mass, DEI) found 364.1316 M$^+$, calculated for $C_{22}H_{20}O_5$ 366 1311.

EXAMPLE 6

Synthesis of Compound II ($C_{21}H_{16}O_5$)

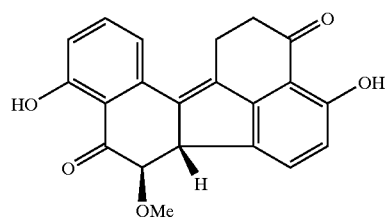

Compound (Ia) (20 mg, 0.06 mmol) was dissolved in dichloromethane (15 mL) and to this was added manganese dioxide (300 mg, 3.4 mmol) in one portion. The reaction was stirred for 24 h at 25° C. and was then filtered through Celite. The filtrate was concentrated in vacuo and purified by preparative HPLC (C18 column, 2.5×30 cm, 70% acetonitrile/water, 25 mL/min., detection at 210 nm). Analytical HPLC (C18 column, 0.8×10 cm, 70% acetonitrile/water, 2 mL/min., PDA detection) of the reaction prior to purification gave product (3.40 min.) with no evidence of any starting material. Compound II (4 mg, 20%) was obtained as a yellow powder following lyophilisation.

$^1$H NMR (400 MHz, CDCl$_3$) 12.22 (1H, s), 10.62 (1H, s), 7.75 (1H, d, 8.2), 7.54 (1H, t, 8.0), 7.11 (1H, d, 7.8), 6.93 (1H, dd, 8.4, <1), 6.82 (1H, d, 8.2), 4.13 (1H, dt, 12.7, 2.5), 3.75 (3H, s), 3.59 (1H, d, 12.7), 3.47–3.28 (2H, m), 2.98–2.85 (2H, m); MS (accurate mass, DEI) found 348.0994 M$^+$, calculated for C$_{21}$H$_{16}$O$_5$ 348.0998.

EXAMPLE 7

Synthesis of Compound 5 (C$_{24}$H$_{25}$NO$_4$)

Compound (Ia) (10 mg, 0.028 mmol) was dissolved in methanol (7 mL) and to this was added cyclopropylamine (100 μL, 1.4 mmol). The reaction was stirred for 10 min. at 25° C. before adding sodium cyanoborohydride (20 mg, 0.32 mmol). The pH of the reaction was then adjusted to 5 (paper) using glacial acetic acid and stirring was continued at 25° C. for 8 h. After this time, the reaction was concentrated in vacuo and the residue was dissolved in dichloromethane. This solution was extracted with water and saturated brine before being dried (MgSO$_4$), filtered and concentrated in vacuo. Analytical HPLC (C18 column, 0.8×10 cm ) did not succeed in separating the two C3 diastereoisomers, which were of sufficient purity to be analysed directly by $^1$H NMR spectroscopy.

Two diastereoisomers were produced (9 mg, 80%). The major one made up 74% of the product, the minor one 26% as calculated by $^1$H NMR spectroscopy.

$^1$H NMR (400 MHz, d4-MeOH) δ 7.44 (1H minor, d, 8.0), 7.39 (1H major, d, 7.9), 7.31–7.25 (1H major 2H minor, m), 7.15 (1H major, d, 7.7), 6.83 (1H major 1H minor, m), 6.64 (1H minor, d, 7.9), 6.56 (1H major, d, 8.0), 5.59 (1H minor 1H major, m), 4.40 (1H minor, t, 5.1), 4.35 (1H major, dd, 10.5, 4.1), 4.13–4.03 (1H major 1H minor, m), 3.58 (3H minor, s), 3.56 (3H major, s), 3.34–3.22 (1H minor, m), 3.20–3.12 (1H major, m), 3.09–3.03 (1H major 1H minor, m), 2.98–2.81 (1H major 1H minor, m), 2.73–2.65 (1H major, m), 2.61–2.55 (1H major 1H minor, m), 2.32–2.25 (2H minor, m), 1.85–1.74 (1H major, m), 0.85–0.59 (4H minor 4H major, m); MS (DCI+NH$_3$) found 392 (MH+), C$_{24}$H$_{25}$NO$_4$ requires Mr 391.

EXAMPLE 8

Synthesis of Compound 6 (C$_{28}$H$_{27}$NO$_4$)

The reductive amination as described in Example 7 was carried out with benzylamine instead of cyclopropylamine, but otherwise under identical reaction conditions to those outlined in that Example. Only one isomer (3.4 mg, 27%) was produced in the reaction following purification by preparative HPLC (C18 column, 2.5×30 cm, 55% acetonitrile/water, 25 mL/min., detection at 210 nm).

$^1$H NMR (400 MHz, d4-MeOH) δ 7.51–7.34 (6H, m), 7.28 (1H, t, 7.9), 7.15 (1H, d, 7.7), 6.82 (1H, d, 7.4), 6.58 (1H, d, 7.9), 5.59 (1H, d, 3.4), 4.34 (1H, dd, 10.8, 4.0), 4.15 (1H, d, 12.8), 4.08 (1H, dd, 11.8, 3.1), 4.00 (1H, d, 12.8), 3.57 (3H, s), 3.24–3.14 (1H, m), 3.07 (1H, dd, 11.8, 3.4), 2.96–2.84 (1H, m), 2.69–2.61 (1H, m), 1.89–1.77 (1H, m); MS (DCI+NH$_3$) found 442 (MH+), C$_{28}$H$_{27}$NO$_4$ requires Mr 441.

EXAMPLE 9

Synthesis of Compound 7 (C$_{21}$H$_{19}$NO$_5$)

Hydroxylamine.HCl salt (250 mg, 3.6 mmol) was dissolved in the minimum volume of 2N aqueous sodium hydroxide solution until the pH was 5 (paper). Compound (Ia)(10 mg, 0.028 mmol) was added to this solution in methanol (4 mL) and the reaction was left to stir at 25° C. After three hours, the initially yellow coloured solution had turned colourless and stirring was continued for a total of 22 h. After this time, the methanol was removed in vacuo and the residue was taken up in dichloromethane. This was extracted with water and saturated brine before being dried (MgSo$_4$), filtered and concentrated. Yield 8 mg, 77%.

At this stage the compound was sufficiently pure for $^1$H NMR analysis, or it could be purified further by preparative HPLC (C18 column, 2.5×30 cm, 40% acetonitrile/water, 25 mL/min., detection at 210 nm).

$^1$H NMR (400 MHz, CDCl$_3$) d 9.81 (1H, br.s), 7.51 (1H, d, 7.8) 7.29 (1H, t, 7.9), 7.19 (1H, d, 7.5), 7.08 (1H, s), 6.87 (1H, d, 7.2), 6.79 (1H, d, 8.0), 6.16 (1H, br.s), 5.36 (1H, d, 4.3), 3.91 (1H, dt, 11.9, 2.3), 3.55 (3H, s), 3.39 (1H, dt, 16.8, 6.2), 3.25 (1H, s), 3.18 (1H, dd, 12.0, 4.3), 3.17–3.10 (2H, m), 2.79 (1H, dt, 16.7, 8.4); MS (DCI+NH$_3$) found 366 (MH+), C$_{21}$H$_{19}$NO$_5$ requires Mr 365.

EXAMPLE 10

Synthesis of Compound 8 (C$_{21}$H$_{17}$ClO$_5$)

Compound (Ia) (20 mg, 0.06 mmol) was dissolved in thionyl chloride at 25° C. and stirred at this temperature for 4 h. After this time, the thionyl chloride was removed in vacuo and the residue was dissolved in acetonitrile:water (1:1) before being analysed by HPLC (C18 column, 0.8×10 cm, 50% acetonitrile/water, 2 mL/min., PDA detection). Two peaks were identified (3.19 min., XR774) and 4.52 min. The crude product was purified by preparative HPLC (C18 column, 2.5×30 cm, 50% acetonitrile/water, 25 mL/min., detection at 210 nm) and lyophilised to give a yellow powder, 3 mg (14%).

$^1$H NMR (400 MHz, CDCl$_3$) d 11.12 (1H, s), 7.78 (1H, s), 7.31 (1H, t, 7.9), 7.2 (1H, d, 7.7), 6.91 (1H, d, 7.8), 6.07 (1H, s), 5.40 (1H, d, 4.2), 4.01 (1H, br.d, 11.7); MS (DCI+NH$_3$) found 385/387, 3:1 ratio (MH+), C$_{21}$H$_{17}$ClO$_5$ requires 384/386 (M$_r$), 3:1 ratio.

EXAMPLE 11

Synthesis of Compound 9 C$_{24}$H$_{24}$O$_5$

Compound (Ia)(20 mg, 0.06 mmol) was dissolved in n-propanol (2.5 mL) before adding 1 drop of concentrated sulfuric acid from a Pasteur pipette. The reaction was stirred at 25° C. for 2 h and then neutralised (pH paper) with aqueous sodium hydroxide solution (2N). Analytical HPLC (C18 column, 0.8×10 cm, 70% acetonitrile/water, 2 mL/min., PDA detection) of the reaction gave one main peak at 3.40 min. with no evidence of starting material. The crude ether was then purified by preparative HPLC (C18 column, 2.5×30 cm, 70% acetonitrile/water, 25 mL/min., detection at 210 nm) to afford, after lyophilisation, a fine yellow powder (8 mg, 36%)

$^1$H NMR (400 MHz, d4-MeOH) δ 7.80 (1H, d, 8.2), 7.31 (2H, m) 6.91–6.86 (1H, m), 6.76 (1H, d, 8.2), 5.41 (1H, d, 2.9), 4.18 (1H, dt, 11.6, ~1), 4.04 (1H, dt, 9.0, 6.7), 3.89 (1H, dt, 9.0, 6.9), 3.58 (3H, s), 3.57–3.44 (1H, m), 3.33–3.22 (1H, m), 3.21 (1H, dd, 11.7, 2.9), 3.00–2.88 (2H, m), 1.77–1.66 (2H, m), 1.01 (3H, t, 7.4); LC-MS (TMD) found 392 (M+), C$_{24}$H$_{24}$O$_5$ requires 392 (M$_r$).

EXAMPLE 12

Synthesis of Compounds 10 and 11 ($C_{23}H_{22}O_5$ and $C_{22}H_{20}O_5$) and Inverted Isomers Thereof The procedure of Example 11 was used with ethanol and methanol as solvent to prepare the ethyl and methyl ethers in 78% and 88% yield respectively. Analytical HPLC (C18 column, 0.8×10 cm, 60% acetonitrile/water, 2 mL/min., PDA detection) gave retention times of 3.70 min. (ethyl ether) and 2.65 min. (methyl ether). Both these compounds were then purified by preparative HPLC (C18 column, 2.5×30 cm, 60% acetonitrile/water, 25 mL/min., detection at 210 nm).

Compound 10 (ethyl ether)

$^1$H NMR (400 MHz, CDCl$_3$) δ 10.62 (1H, s), 7.78 (1H, d, 8.2), 7.27 (1H, t, 7.8), 7.23 (1H, d, 7.6), 6.80 (1H, dd, 7.6, 1.1), 6.74 (1H, d, 8.3), 5.82 (1H, s), 5.28 (1H, d, 3.9), 4.24 (1H, dt, 11.8, ~2), 4.03–3.95 (1H, m), 3.95–3.87 (1H, m), 3.53 (3H, s), 3.42–3.32 (1H, m), 3.28–3.21 (1H, m), 3.19 (1H, dd, 11.8, 3.9), 2.94–2.79 (2H, m), 1.27 (3H, t, 7.1); MS (accurate mass DEI), found 378.1467 M$^+$, calculated for $C_{23}H_{22}O_5$ 378.1468.

Compound 11 (methyl ether)

$^1$H NMR (400 MHz, CDCl$_3$) δ 10.62 (1H, s), 7.79 (1H, d, 8.2), 7.29–7.23 (2H, m), 6.78 (1H, dd, 7.0, 2.0), 6.74 (1H, d, 8.3), 5.52 (1H, s), 5.21 (1H, d, 3.6), 4.29 (1H, dt, 11.8, ~2), 3.71 (3H, s), 3.55 (3H, s), 3.42–3.33 (1H, m), 3.28–3.21 (1H, m), 3.20 (1H, dd, 11.8, 3.7), 2.94–2.79 (2H, m); MS (accurate mass DEI), found 364.1311 M$^+$, calculated for $C_{22}H_{20}O_5$ 364.1311.

From the reactions with the methanol and ethanol, two further compounds were isolated by HPLC (conditions above) which were characterised as the inverted methyl and ethyl ether derivatives respectively. Analytical HPLC (C18 column, 0.8×10 cm, 60% acetonitrile/water, 2 mL/min., PDA detection) gave retention times of 7.46 min. (inverted ethyl ether, compound 10a) and 4.51 min. (inverted methyl ether, compound 11a). The quantity of each was less than 5 mg.

Compound 11a

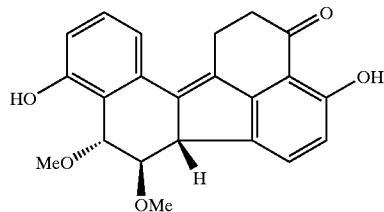

$^1$H NMR (400 MHz, CDCl$_3$) δ 10.7 (1H, s), 8.36 (1H, s), 7.74 (1H, d, 8.2), 7.31 (1H, t, 7.9), 7.14 (1H, dd, 7.9, <1), 6.89 (1H, dd, 7.9, <1), 6.78 (1H, d, 8.2), 5.27 (1H, d, 8.2), 3.66 (3H, s), 3.66–3.62 (1H, m), 3.45 (1H, dd, 11.8, 8.2), 3.38 (3H, s), 3.37–3.25 (2H, m), 2.94–2.89 (2H, m) ; MS (accurate mass DEI), found 364.1304 M$^+$, calculated for $C_{22}H_{20}O_5$ 364.1311.

Componund 10a

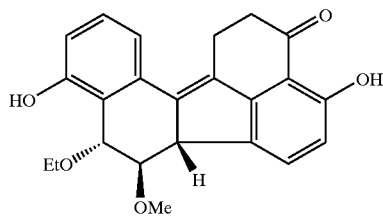

$^1$H NMR (400 MHz, CDCl$_3$) δ 10.7 (1H, s), 8.50 (1H, s), 7.75 (1H, d, 8.2), 7.29 (1H, t, 7.9), 7.13 (1H, d, 7.9), 6.89 (1H, dd, 7.9, <1), 6.78 (1H, d, 8.3), 5.26 (1H, d, 8.2), 3.65 (3H, s), 3.65–3.51 (3H, m), 3.44 (1H, dd, 11.8, 8.1), 3.40–3.23 (2H, m), 2.94–2.88 (2H, m), 1.29 (3H, t, 7.1) ); MS (accurate mass DEI), found 378.1462 M$^+$, calculated for $C_{23}H_{22}O_5$ 378.1468.

EXAMPLE 13

Synthesis of Compounds 12 and 13

Compound (Ia) (50 mg, 0.14 mmol) was dissolved in dichloromethane (50 mL) and N-bromosuccinimide (50 mg, 0.28 mmol) was added in one portion. The reaction was stirred at 25° C. for 16 h and was then washed with water and saturated brine. The reaction was repeated using the same quantities of XR774 and NBS, but limiting the reaction time to 3 h at 25° C. The combined organic fractions of these two experiments following work-up were then dried (MgSO$_4$), filtered and concentrated in vacuo.

Analytical HPLC (C18 column, 0.8×10 cm, 50% acetonitrile/water, 2 mL/min., PDA detection) indicated 4 products were present with retention times of 3.33 min., 3.80 min., 5.90 min. and 7.16 min. Compound Ia was retained less by the column under these conditions, having a retention time of 2.26 min. The crude products were purified by preparative HPLC (C18 column, 2.5×30 cm, 50% acetonitrile/water then 60% acetonitrile/water after the elution of the second product, 25 mL/min., detection at 210 nm). The following compounds were all obtained as yellow powders following lyophilisation.

12a ($C_{21}H_{17}BrO_5$)

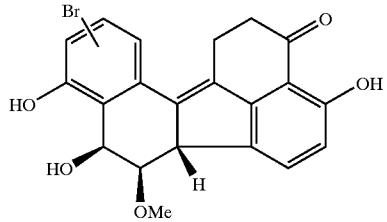

$^1$H NMR (400 MHz, d4-MeOH) δ 7.80 (1H, d, 8.1), 7.54 (1H, d, 8.8), 6.85 (1H, d, 8.8), 6.82 (1H, d, 8.2), 5.58 (1H, d, 3.7), 4.19 (1H, dt, 10.8, <1), 3.73–3.65 (1H, m), 3.51 (3H, s), 3.00–2.78 (4H, m); MS (DCI+NH$_3$) found 429/431, 1:1 ratio (MH+), $C_{21}H_{17}BrO_5$ requires 428/430 (M$_r$) 1:1 ratio.

12b ($C_{21}H_{17}BrO_5$)

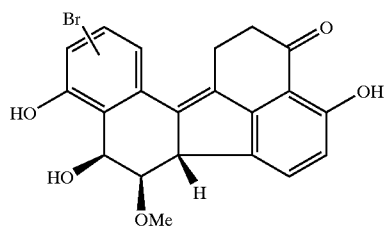

$^1$H NMR (400 MHz, d4-MeOH) δ 7.81 (1H, d, 8.3), 7.63 (1H, d, 8.4), 7.29 (1H, d, 8.5), 6.79 (1H, d, 8.1), 5.67 (1H, d, 3.3) 4.25 (1H, dt, 11.7, ~2), 3.61 (3H, s), 3.59–3.44 (1H, m), 3.35–3.24 (1H, m), 3.20 (1H, dd, 11.7, 3.2), 3.03–2.89 (2H, m) ; MS (DCI +$NH_3$) found 429/431, 1:1 ratio (MH+), $C_{21}H_{17}BrO_5$ requires 428/430 ($M_r$) 1:1 ratio.

13a ($C_{21}H_{16}Br_2O_5$)

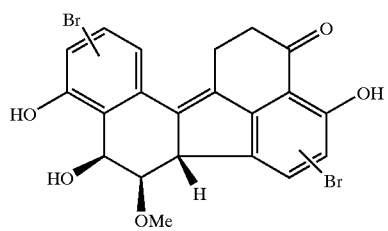

$^1$H NMR (400 MHz, d4-MeOH) δ 8.00 (1H, s), 7.63 (1H, d, 8.4), 7.29 (1H, d, 8.5), 5.69 (1H, d, 3.3), 4.27 (1H, dt, 11.8, ~2), 3.62 (3H, s), 3.59–3.48 (1H, m), 3.37–3.28 (1H, m), 3.23 (1H, d, 11.7, 3.3), 3.04–2.95 (2H, m); MS (DCI+$NH_3$) found 507/509/511, 1:2:1 ratio (MH+), $C_{21}H_{16}Br_2O_5$ requires $M_r$ 508.

13b ($C_{21}H_{16}Br_2O_5$)

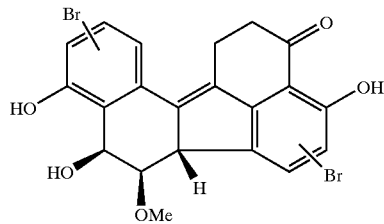

$^1$H NMR (400 MHz, d4-MeOH) δ 7.87 (1H, s), 7.80 (1H, d, 8.3), 6.84 (1H, d, 8.2), 5.50 (1H, d, 3.7), 4.13 (1H, dt, 9.9, ~2), 3.68–3.59 (1H, m), 3.53 (3H, s), 3.06 (1H, dd, 9.8, 3.8), 3.001–2.79 (3H, m); MS (DCI+$NH_3$) found 507/509/511, 1:2:1 ratio (MH+), $C_{21}H_{16}Br_2O_5$ requires $M_r$ 508.

EXAMPLE 14

Cytokine Release From Jurkat E6-1 Cells

Jurkat E6-1 cell line was obtained from American Tissue Culture Collection (ATCC, Rockville, USA). The cells were pre-treated with 3 ng/ml phorbol myristate acetate (PMA) for three hours, washed and exposed to dose ranges of the compound to be tested followed by the addition of 5 µg/ml anti-CD28.

After 18 hours incubation at 37° C. and 5% $CO_2$, cell culture supernatants were harvested for determination of IL-2 secretion by Dissociation Enhanced Lanthanide Fluorescence Immuno Assay (DELFIA). The effect of compound on cell cytotoxicity was determined using a redox potential sensitive dye, resazurin. Effects on protein synthesis were determined by investigation of [$^3$H] leucine uptake.

In this test compound (Ia) inhibited IL-2 release at concentration between 0.06 to 7 µM, as shown in Table 4. At this concentration range the compounds were not toxic and showed no effect on protein synthesis.

TABLE 4

| Concentration (µM) | % Inhibition of anti-CD28 induced IL-2 by PMA pre-treated Jurkat E6-1 |
|---|---|
| 7.1 | 91.5 |
| 3.6 | 89.1 |
| 1.8 | 92.2 |
| 0.89 | 85.4 |
| 0.44 | 57.8 |
| 0.22 | 36.0 |
| 0.11 | 30.5 |
| 0.056 | 29.0 |

The $IC_{50}$ of compounds of the invention for the inhibition of anti-CD28 induced IL-2 production by Jurkat E6-1 cells is shown in Table 5:

TABLE 5

| Compound | $IC_{50}$/µM |
|---|---|
| (Ia) | 0.34 |
| (Ib) | 2.5 |
| (II) | >5.0 |
| (III) | 4.3 |
| 2a | 2.96 |
| 3 | >9.56 |
| 4 | 6.64 |
| 5 | 1.28 |
| 7 | >1.49 |
| 9 | 10.93 |
| 10 | 2.35 |
| 11 | 1.06 |
| 10a | >7.94 |
| 11a | >6.18 |
| 12a | 1.42 |
| 12b | 7.34 |
| 13a | >4.91 |

EXAMPLE 15

Cytokine Release From T Cells

The effect of compound (Ia) on IL-2 release was investigated using a previously described method (Van Cool S. W. et al., (1993) J. Immunol. 150: 3254–3263). T cells were purified by depletion of B cells and monocytes from Buffy coats obtained from normal healthy donors following separation of human peripheral blood mononuclear cells (PBMC) on Lymphoprep. Purified T cells were suspended in RPMI 1640 supplemented with 5% fetal bovine serum (FBS) and aliquoted into 96 well plates coated with anti-CD3. Cells were exposed to dose ranges of the compound to be tested followed by the addition of 5 µg/ml anti-CD28 and incubated for 18 hours at 37° C. and 5% $CO_2$. IL-2 secretion in cell culture supernatants was determined using IL-2 DELFIA.

Compound Ia inhibited the secretion of IL-2 at concentrations between 0.06 to 7 μM, as shown in Table 6. At this dose range the compound was not toxic to T cells. The $IC_{50}$ (μM) of compound (Ia) for inhibition of anti-CD3 and anti-CD28 induced IL2 production by T cells is 0.12.

TABLE 6

| Concentration (mM) | % Inhibition of anti-CD-28 and Anti-CD3 induced IL-2 by T cells |
|---|---|
| 7.1 | 100.5 |
| 3.6 | 100 |
| 1.8 | 100 |
| 0.89 | 98.6 |
| 0.44 | 88.3 |
| 0.22 | 105.9 |
| 0.11 | 47.3 |
| 0.056 | 29.8 |

EXAMPLE 16

Cytokine Release From Monocytes

The effect of compound (Ia) on TNF-α release was investigated using a previously described method (Bakouche, O. et al., (1992), J. Immunol: 14, 84–91). Human monocytes were purified by elutriation from Buffy coats obtained from normal healthy donors after the separation of peripheral blood mononuclear cells (PBMC) on Lymphoprep. The monocytes were suspended in RPMI 1640 with 5% FBS and exposed to dose ranges of the compound to be tested followed by the addition of 1 ng/ml LPS. After incubation for 18 hours at 37° C. and 5% $CO_2$ cell culture supernatants were harvested and stored at –70° C. Effects on TNF-α release were determined using a DELFIA.

Compound (Ia) inhibited the secretion of TNF-α at concentrations between 0.1 to 5.7 μM, as shown in Table 7. At this dose range the compounds were not toxic to monocytes. The $IC_{50}$ (μM) value of compound (Ia) for inhibition of LPS induced TNF-α secretion by monocytes is 0.42.

TABLE 7

| Concentration (mM) | % Inhibition of LPS induced TNF-a by monocytes |
|---|---|
| 5.7 | 89 |
| 2.9 | 80 |
| 1.4 | 73.2 |
| 0.7 | 57.6 |
| 0.36 | 48.1 |
| 0.18 | 32.1 |
| 0.09 | 19 |

EXAMPLE 17

Cytokine Release From Whole Blood

Whole blood samples obtained from up to seven normal healthy volunteers were diluted in an equal volume of RPMI 1640 with 5% FBS and exposed to dose ranges of compound (Ia) followed by the addition of 10 μg/ml phytohaemagglutinin (PHA) and 100 ng/ml LPS. After incubation for 48 hours at 37° C. and 5% $CO_2$ serum samples were harvested for determination of effect on IL-2 and TNF-α secretion using DELFIAs specific for each cytokine respectively.

Compound (Ia) inhibited both IL-2 and TNF-α release from PHA and LPS stimulated whole blood at concentrations between 0.1 to 7 μM. The $IC_{50}$ values of compound (Ia) for inhibition of IL-2 and TNF-α production by separate donors are shown in Table 8.

TABLE 8

| | $IC_{50}$ (μM) | |
|---|---|---|
| Whole Blood | Inhibition of TNF-α | Inhibition of IL-2 |
| Donor 1 | 14 | 0.22 |
| Donor 2 | 14 | 1.2 |
| Donor 3 | 0.7 | 0.43 |
| Donor 4 | >2.7 | >2.7 |
| Donor 5 | 5.3 | <0.4 |
| Donor 6 | 3.0 | <0.4 |

EXAMPLE 18

Inhibition of Tyrosine Kinase Activity

Ten units of recombinant abl kinase was incubated in the presence of 250 nM biotinylated peptide 6-20 p34cdc in a total of 50 μl in a microtitre plate in the presence of ATP and incubated at 37° C. for 3 hours. Phosphorylation of the peptide substrate was detected using a non-separation time resolved fluorescence assay (LANCE™) using anti-phosphotyrosine conjugated europium and streptavidin conjugated allophycocyanin (APC).

As shown in Table 9, compound (Ia) inhibited phosphorylation of the peptide by abl kinase at concentrations between 0.001–5.2 μM. Table 10 shows the $IC_{50}$ (μM) of compound (Ia) and other compounds of the invention in this assay.

TABLE 9

| Concentration of (Ia) (μM) | % Inhibition of tyrosine kinase activity |
|---|---|
| 0.001 | 39 |
| 0.01 | 56.2 |
| 0.081 | 86.3 |
| 0.65 | 98.6 |
| 5.2 | 100.3 |

TABLE 10

| Compound | $IC_{50}$ |
|---|---|
| Ia | 0.006 |
| 2a (major isomer) | >1 |
| 2b (minor isomer) | >1 |
| 3 | 0.7 |
| 4 | >1 |
| II | >5 |
| 5 | >1 |
| 7 | >1 |
| 8 | >1 |
| 9 | 0.132 |
| 10 | 0.274 |
| 11 | 0.045 |
| 10a | >5 |
| 11a | 2.36 |

EXAMPLE 19

Pharmaceutical Composition

Tablets, each weighing 0.15 g and containing 25 mg of a compound of formula (I), (II) or (III) can be manufactured as follows:

Composition for 10,000 Tablets compound of formula (I), (II) or (III) (250 g)

lactose (800 g)

corn starch (415 g)

talc powder (30 g)

magnesium stearate (5 g)

The compound of formula (I), (II) or (III), lactose and half of the corn starch are mixed. The mixture is then forced through a sieve 0.5 mm mesh size. Corn starch (10 g) is suspended in warm water (90 ml). The resulting paste is used to granulate the powder. The granulate is dried and broken up into small fragments on a sieve of 1.4 mm mesh size. The remaining quantity of starch, talc and magnesium stearate is added, carefully mixed and processed into tablets.

What is claimed is:

1. A compound of formula (I):

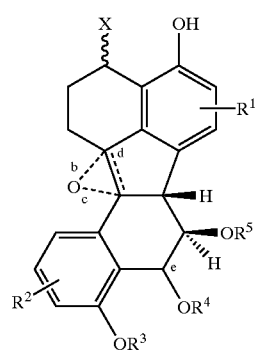

(I)

wherein ⁓X is =O, N—OR$^6$, —$^a$—NHR or —$^a$—OH wherein R$^6$ is H or $C_1$–$C_6$ alkyl, bond a is oriented ◀ or ⦀⦀⦀ and R is H, $C_1$–$C_6$ alkyl which is unsubstituted or substituted by $C_6$–$C_{10}$ aryl, or $C_3$–$C_6$ cycloalkyl;

—$^b$— is a bond and —$^b$— and —$^c$— are not bonds or, when X is =O, —$^b$— and —$^c$— are both bonds and —$^d$— is not a bond;

R$^1$ and R$^2$, which is the same or different, are H or a halogen;

R$^3$ and R$^4$, which are the same or different, are H, $C_1$–$C_6$ alkyl, $C_3$–$C_6$ cycloalkyl, a heterocyclic group or an aromatic group;

bond e is oriented ◀ or ⦀⦀⦀; and

R$^5$ is $C_1$–$C_6$ alkyl;

or formula (Ib):

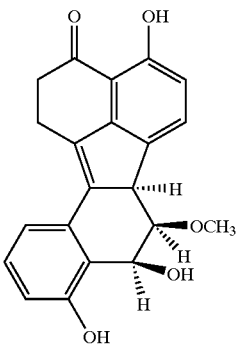

(Ib)

or formula (II):

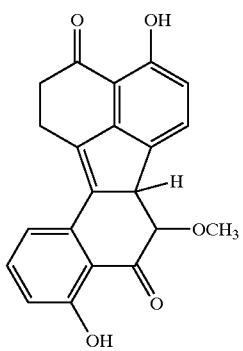

(II)

or formula (III):

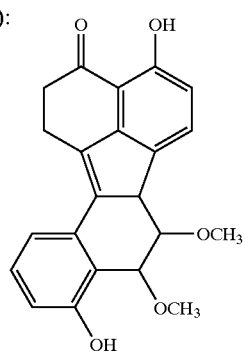

(III)

or a stereoisomer of a said compound; or a pharmaceutically acceptable salt or ester of a said compound or said stereoiaomer.

2. A compound according to claim 1 which is of formula (I'):

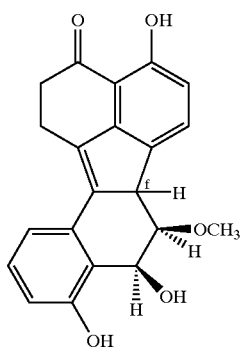

(I')

wherein bond f is oriented ◀ or ⦀⦀⦀; or which is a compound or formula (II) or (III) as defined in claim 1.

3. A compound according to claim 1 or 2 which has the following formula (Ia):

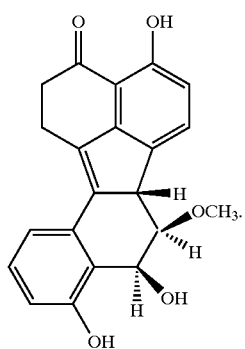

(Ia)

4. A pharmaceutical or veterinary composition comprising a pharmaceutically or veterinarily acceptable carrier or diluent and, as active ingredient, a compound as defined in claim 1.

5. A process for producing a compound as defined in claim 1, which process comprises:

(a) treating a compound of formula (Ia)

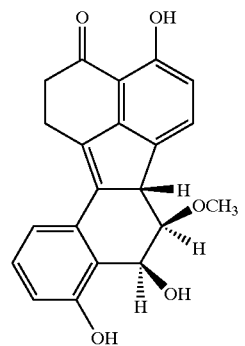

(Ia)

with an amine of formula R'—$NH_2$ in which R' is H, $C_1$–$C_6$ alkyl which is unsubstituted or substituted by $C_6$–$C_{10}$ aryl, or $C_3$–$C_6$ cycloalkyl, in water or an organic solvent in the presence of a reducing agent at a pH of from 5 to 6, to obtain a compound of formula (I)

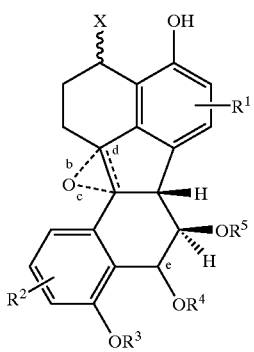

(I)

in which ⌇⌇X is —ᵃ—NHR; or (b) treating a compound of formula (Ia) with a halogenating agent to obtain a compound of formula (I) in which one or both of $R^1$ and $R^2$ is a halogen; or (c) treating a compound of formula (Ia) with an alcohol of formula $R^4$—OH in which $R^4$ is other than hydrogen, in the presence of an acid, to obtain a compound of formula (I); or (d) treating a compound of formula (Ia) with a halide of formula $R^3$—Y, wherein Y is a halogen, in an organic solvent in the presence of a base and, optionally, a quaternary ammonium halide to obtain a compound of formula (I); or (e) treating a compound of formula (Ia) with hydroxylamine or an organic solvent and/or water to obtain a compound of formula (I) in which ⌇⌇X is =N—OH; or (f) treating a compound of formula (Ia) with a peracid in an organic solvent to give a compound of formula (I) in which —ᵇ— and —ᶜ— are both bonds and —ᵈ— is not a bond; or (g) treating a compound of formula (Ia) with a reducing agent in an organic solvent to give a compound of formula (I) in which ⌇⌇X is —ᵃ—OH; or (h) treating a compound of formula (Ia) with an oxidising agent to obtain a compound of formula (II)

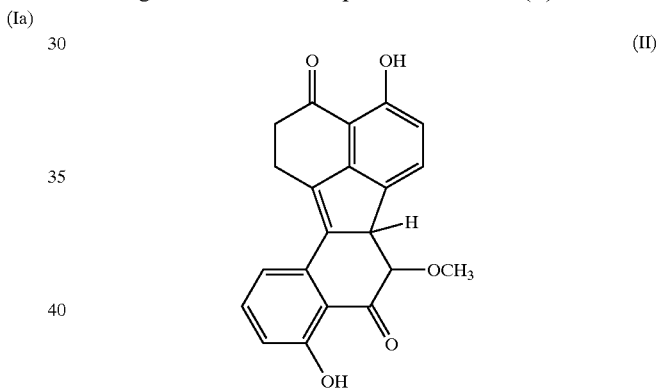

(II)

in which the groups —H and —$OCH_3$ are both oriented ◀; and (i) converting a compound obtained in any one of steps (a) to (h) into a pharmaceutically acceptable salt or ester.

6. A process for producing a compound as defined in claim 2, which process comprises (i) fermenting, in a fermentation medium which provides a source of carbon, nitrogen and inorganic salts, fungal strain X20700 (CBS 100220) or a mutant thereof which produces the said compound; and (ii) isolating the said compound from the fermentation medium.

7. A biologically pure culture of the fungal strain *Cladosporium* cf. *cladosporioides* X20700 (CBS 100220) or of a mutant thereof which produces a compound as defined in claim 2.

8. A process for fermenting fungal strain *Cladosporium* cf. *cladosporioides* X20700 (CBS 100220) or a mutant thereof which produces a compound as defined in claim 2, which process comprises fermenting the said fungal strain or said mutant in a fermentation medium which provides a source of carbon, nitrogen and inorganic salts.

9. A method of treating a patient in need of a cytokine production inhibitor or a tyrosine kinase inhibitor, which method comprises administering to the patient a therapeutically effective amount of a compound as defined in claim 1.

10. A method of treating an immunoinflammatory condition selected from rheumatoid arthritis, osteoarthritis, septic shock, psoriasis, inflammatory bowel disease, Crohn's disease systemic lupus erythematosus, (SLE), multiple sclerosis, diabetes and asthma, which method comprises administering to a patient in need thereof a therapeutically effective amount of a compound as defined in claim 1.

11. A method of treating cancer, which method comprises administering to a patient in need thereof a therapeutically effective amount of a compound as defined in claim 1.

* * * * *